Figure 1:
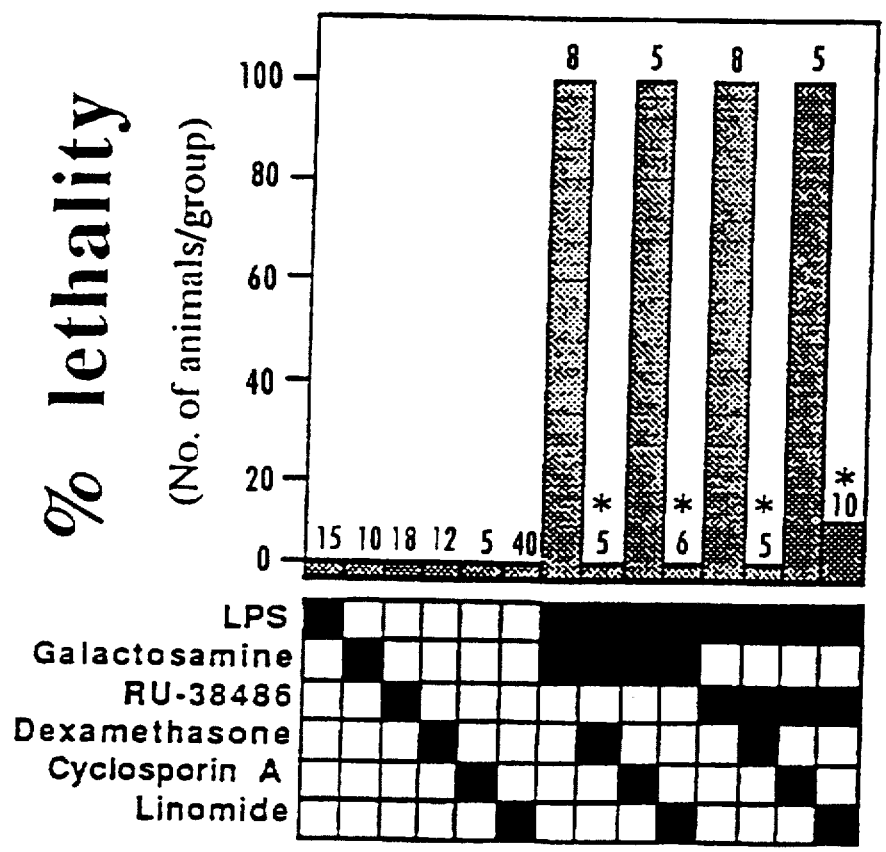

US005776947A

United States Patent [19]
Kroemer et al.

[11] Patent Number: 5,776,947
[45] Date of Patent: Jul. 7, 1998

[54] USE OF QUINOLINE-3-CARBOXAMIDE COMPOUNDS FOR INHIBITING THE PRODUCTION OF TUMOR NECROSIS FACTOR (TNF) AND/OR FOR THE TREATMENT OF SEPTIC SHOCK

[75] Inventors: Guido Peter Kroemer; JoséAngel Gonzalo; Carlos Martinez Alonso, all of Madrid, Spain; Terje Kalland, Löddeköpinge, Sweden

[73] Assignee: Pharmacia AB, Stockholm, Sweden

[21] Appl. No.: 586,857

[22] PCT Filed: Jun. 10, 1994

[86] PCT No.: PCT/SE94/00565
§ 371 Date: May 20, 1996
§ 102(e) Date: May 20, 1996

[87] PCT Pub. No.: WO95/03051
PCT Pub. Date: Feb. 2, 1995

[30] Foreign Application Priority Data

Jul. 26, 1993 [SE] Sweden ................... 9302490

[51] Int. Cl.$^6$ ................................................. A61K 31/47
[52] U.S. Cl. .................................. 514/312; 514/313
[58] Field of Search .............................. 514/312, 313

[56] References Cited

U.S. PATENT DOCUMENTS 4,547,511  10/1985  Erikskoo ........................... 514/312

FOREIGN PATENT DOCUMENTS 9306829  4/1993  WIPO .

OTHER PUBLICATIONS

Scand J Infect Dis–Suppl., vol. 88, Apr. 1993, Nils–Gunnar Ilbäck et al, "Effects of the Antiviral WIN 54954 and the Immune Modulator LS 2616 on Cachetin/TNF and gamma–interferon Responses during Viral Heart Disease" p. 117–p. 123.
Eur. J. Immunol., vol. 23, Sep. 1993, J.A. Gonzalo et al, "Linomide, a novel immunomodulator that prevents death in four models of septic shock" p. 2372 –p. 2374.
The Toxcicity of Staphylococcal Enterotoxin B in Mice is Mediated by T Cells, by Philippa et al., J. Exp. Med. © The Rockefeller University Press, vol. 171 Feb. 1990 455–464.
T Cell–mediated Lethal Shock Triggered in Mice by the Superantigen Staphyloccal Enterotoxin B: Critical Role of Tumor Necrosis Factor, by Thomas Miethke et al., J. Exp. Med. © The Rockefeller University Press, vol. 175 Jan. 1992 91–98.
Septic Shock: pathogenesis, by M.P. Glauser, G. Zanetti et al., The Lancet, vol. 338: Sep. 21, 1991 pp. 732–739.
The Pathophysiology of Tumor Necrosis Factors, by Pierre Vassalli, Annu. Rev. Immunol. 1992, 10:411–52.
Passive Immunization Against Cachectin/Tumor Necrosis Factor Protects Mice From Lethal Effect of Endotoxin, by B. Beutler et al., Science, 30 Aug. 1985, pp. 869–871.

Anti–cachectin/TNF monoclonal antibodies prevent septic shock during lethal bacteraemia, by Kevin J. Tracey et al., Nature, vol. 330, 17 Dec. 1987, pp. 662–664.
Interferon–α prevents endotoxin–induced mortality in mice, by Shie–Pon Tzung et al., Eur. J. Immunol. 1992, 22: 3097–3101.
Interlukin 10 Reduces the Release of Tumor Necrosis Factor and Prevents Lethality in Experimental Endotoxemia, by Catherine Gérard et al., J. Exp. Med. © The Rockefeller University Press, vol. 177 Feb. 1993 547–550.
The effect of adrenalectomy on interleukin–1 release in vitro and in vivo, Mauro Perretti et al., J. Pharmacol. (1989), 98, 1137–1142.
Glucocorticoid–mediated Control of the Activation and Clonal Deletion of Peripheral T Cells In Vivo, by José Angel Gonzalo et al., J.Exp. Med. © The Rockefeller University Press, vol. 177, May 1993 1239–1246.
Cytokine Release Syndrome Induced by the 145 2C11 Anti–CD3 Monoclonal Antibody in Mice: Prevention by High Doses of Methylprednisolone, by Maria–Luisa Alegre et al., The Journal of Immunology, vol. 146m 1184–1191, No. 4, Feb. 15, 1991.
Adrenalectomy Sensitizes Mice to The Lethal Effects of Interleukin 1 and Tumor Necrosis Factor, by Riccardo Bertini et al., J. Exp. Med. © The Rockefeller University Press, vol. 167, May 1988, 1078–1712.
The glucocortocoid antagonist RU38486 mimics interleukin–1 in its sensitization to the lethal and interleukin–6–inducing properties of tumor necrosis factor, by Peter Brouckaert et al., Eur. J Immunol. 1992, 22:981–986.
Programmed cell death and extrathymic reduction of Vβ$^+$CD4$^+$T cells in mice tolerant to *Staphylococcus aureus* enterotoxin B, by Jojiro Kawabe & Atsuo Ochi, Nature, Vo. 349, 17 Jan. 1991, pp. 245–248.

(List continued on next page.)

*Primary Examiner*—Jerome D. Goldberg
*Attorney, Agent, or Firm*—Lowe, Price, LeBlanc & Becker

[57] ABSTRACT

The use of a quinoline-3-carboxamide compound comprising structure (I), optionally with substituents for the hydrogen atoms shown ($H^{1-9}$), and a salt of compound (I) where (a) ---- represents that there are two conjugated double bonds between the atoms comprised by the dashed line, (b) $X_1$ and $X_2$ are separately selected form an oxygen atom or an $NH^9$ group, said $X_1$ and $X_2$ being bound by a single bond to the ring when attached to $H^7$ or $H^8$ and by a double bond when not bound to $H^7$ or $H^8$, (c) $H^{1-9}$; are hydrogens with the provision that $H^9$ is only present when at least one of $X_1$ and $X_2$ is the $NH^9$ group, (d) $H^7$ and $H^8$ are hydrogens that are attached to different atoms selected among $X_1$, $X_2$ and the nitrogen atom (N) in the quinoline ring, for the manufacture of a composition intended for inhibiting the production of tumor necrosis factor TNF in a living body and/or the treatment of septic shock in a living body.

5 Claims, 3 Drawing Sheets

OTHER PUBLICATIONS

Expansion and clonal deletion of peripheral T cells induced by bacterial superantigen is independent of the interleukin–2 pathway, by José Angel Gonzalo et al., Eur. J. Immunol. 1992. 22:1007–1011.

The effects of RU 486 on Immune Function and Steroid–Induced Immunosuppression in Vitro, by Bradley J. Voorhis et al., Journal of Clinical Endocrinology and Metabolism, vol. 69, No. 6, pp. 1195–1199.

Duration of Antagonizing Effect of RU486 on the Agonist Induction of Tyrosine Aminotransferase Via Glucocorticoid Receptor, by Maria Alexandrova, J. Steroid Biochem. Molec. Biol. vol. 41, No. 3–8, pp. 723–725, 1992.

Abolition of the Effect of Cyclosporine On Rat Cardiac Allograft Rejection By The New Immunomodulator LS–2616 (Linomide), by Alkwin Wanders et al., Transplantation, vol. 47, 216–217, No. 2 Feb. 1989, pp. 216–217.

Evidence That LS–2616 (Linomide) Causes Acute Rejection Of Rat Allografts Protected By Cyclosporine but Not of Long–Term Surviving Allografts, by Alkwin Wanders et al., Transplantation, vol. 52, No. 2, pp. 234–238.

The p70 Tumor Necrosis Factor Receptor Mediates Cytotoxicity, by Renu A. Heller et al., Cell, vol. 70, 47–56, Jul. 10, 1992.

Participation and Interactions of neutrophil elastase in haemostatic disorders of patients with severe infections, by R. Seitz et al., Eur. J. Haematol 1987; 38:231–240.

Elastase–$\alpha_1$–proteinase inhibitor: An early indicator of septicemia and bacterial meningitis in children, by Christian P. Speer, M.D. et al., The Journal of Pediatrics, Nov. 1987, pp. 667–671.

The effect of immunomodulating treatment on cutaneious delayed–type hypersensitivity in MRL lpr/lpr/ mice, by H. Carlsten et al., APMIS 97: 728–732, 1989.

Effects of LS–2616 administration upon the autoimmune disease of (NZB×NZW) $F_1$ hybrid mice, by A. Tarkowski et al., Immunology 1986 59 589–594.

Successful Treatment of Autoimmunity in MRL/1 Mice With LS–2616, A New Immunomodulator, by A Tarkowski et al., Arthirits and Rheumatism, vol. 29, No. 11 (Nov 1986).

Granulocyte elastase–$\alpha_1$–antiproteinase complect in cystic fibrosis: Sensitive plasma assay for monitoring pulmonary infections, by Annika Ericsson Hollsing, M.D. et al., The Journal of Pediatrics, Aug. 1987, vol. 111, No. 2, pp. 206–211.

Circulating neutrophil elastase in infectious diseases in geriatric patients, by E.O. Adeyemi et al., Aging, vol. 1, No. 1, pp. 65–70, 1989.

The Proteinase Inhibitor Complexes (Antithrombin III–Thrombin, $\alpha_2$Antiplasmin–Plasmin and $\alpha_1$Antitrypsin–Elastase) in Septicemia, Fulminant Hepatic Failure and Cardiac Shock: Value for Diagnosis and Therapy Control in DIC/F Syndrome, by R. Egbring et al., Behring Inst. Mitt., No. 79, 87–103, (1986).

Pathobiochemistry of Sepsis: Role of Proteinases, Proteinase Inhibitors and Oxidizing Agents, by M. Jochum et al., Behring Inst. Mitt., No. 79, 121–130 (1986).

Mechanism of Action of the New Immunomodulator LS2616 on T Cell Responses, by Eva–Lotta Larsson et al., Int. J. Immunopharmac. vol. 9, No. 4, pp. 425–431, 1987.

Augmentation of Mouse Natural Killer Cell Activity By LS 2616, a New Immunomodulator, by Terje Kalland et al., The Journal of Immunology, vol. 134, No. 6, Jun. 1985 p. 3956–3961.

Regulation of Natural Killer Progenitors Studies with a Novel Immunomodulator with Distinct Effects at the Precurser Level, by Terje Kalland, Immunology, vol. 144, 4472–4476, No. 11, Jun. 1, 1990.

Effects of the Immunomodulator LS 2616 on Growth and Metastasis of the Murine B16–F10 Melanoma, by Terje Kalland, Cancer Research 46, 3018–3022, Jun. 1986.

USE OF QUINOLINE-3-CARBOXAMIDE COMPOUNDS FOR INHIBITING THE PRODUCTION OF TUMOR NECROSIS FACTOR (TNF) AND/OR FOR THE TREATMENT OF SEPTIC SHOCK

The present invention concerns the use of quinoline-3-carboxamide compounds, in particular roquinimex (Linomide®), or a pharmaceutically acceptable salt thereof for inhibiting the production of tumour necrosis factor (TNF) and/or for the treatment of septic shock.

BACKGROUND OF THE INVENTION

Septic shock is a highly lethal disease which is induced by polyclonal stimulators produced by bacteria, namely lipopolysaccharide (LPS, an endotoxin that stimulates B cells and macrophages) and superantigens (exotoxins that stimulate T-cells in a semi-specific fashion) [1, 2], and implies a critical clinical condition for which thus far no effective treatment is available [3, 4]. Septic shock involves a cytokine release syndrome due to a hyperacute activation of inflammatory cells in response to LPS or bacterial superantigen [3], the tumour necrosis factor (TNF) being one of the major pathogenic factors [5].

In addition to septic shock there are a number of serious diseases related to the production of TNF, i. a.

endotoxic shock, enterotoxin related shock, multi-organ failure, side-effects associated with TNF generated during therapy of neoplastic disease, cahexi associated with neoplastic disease, side-effects associated with treatment with anti-lymphocyte serum or antibodies for prevention of graft rejection, meningococcal meningitis, malaria, autoimmune diseases characterized by TNF production.

Antibodies directed against TNF prevent the detrimental effect of superantigen [2], LPS or *Escherichia Coli* inoculation [6, 7]. WO 92/16553 (CENTO-COR INC.) discloses a high-affinity mouse monoclonal antibody, a chimeric antibody and an anti-TNF antibody, all of which can be used for treatment of for example sepsis syndrome.

Application of cytokines that inhibits TNF secretion reduces the toxicity of LPS in vivo [8, 9]. WO 92/01472 (CELLTECH LTD) discloses a new multivalent immunoglobulin used to treat or prevent diseases associated with elevated cytokine levels, for example sepsis.

Quinoline-3-carboxamide compounds have been suggested as pharmaceuticals. The compounds have comprised the structure given in formula I below, optionally with substituents for the hydrogen atoms shown ($H^{1-9}$, where $H^9$ is part of $X_1$ or $X_2$ as shown in (b) below) and, where appropriate, salts of the compounds:

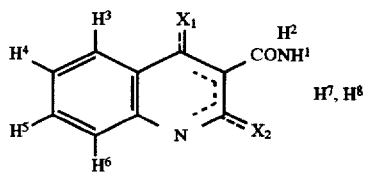

This formula is a collective formula for the tautomeric structures II–IV.

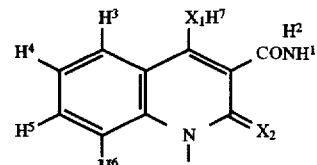

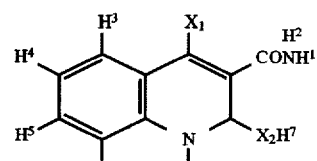

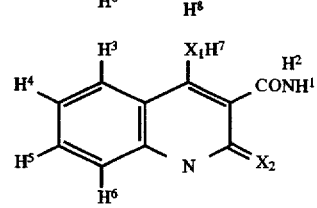

In formula I–IV:

(a) ------- represents that there are two conjugated double bonds between the atoms comprised by the dashed line (only formula I).

(b) $X_1$ and $X_2$ are separately selected from an oxygen atom or an $NH^9$ group that is possibly substituted, said $X_1$ and $X_2$ being bound by a single bond to the ring when attached to $H^7$ or $H^8$ and by a double bond when not bound to $H^7$ or $H^8$.

(c) $H^{1-9}$ are hydrogens, with the provision that $H^9$ is only present when at least one of $X_1$ and $X_2$ is the $NH^9$ group.

(d) $H^7$ and $H^8$ are hydrogens that are attached to different atoms selected among $X_1$, $X_2$ and the nitrogen atom in the quinoline ring said $X_1$ and $X_2$ being bound by a single bond to the ring when attached to $H^7$ or $H^8$ and by a double bond when not bound to $H^7$ or $H^8$.

The substituents that are to replace $H^{1-9}$ may, according to the prior art, comprise any substituent that gives compounds that can be isolated. See for instance Indian Journal of Chemistry Vol 17B (1979) 488–90 (anti-inflammatory properties), U.S. Pat. No. 3,960,868 (=GB 1,467,061, analgesic, anticonceptive, anti-inflammatory and anti-allergic properties), U.S. Pat. Nos. 4,547,511 and 4,738,971 (enhancing cell-mediated immunity), WO 9015052 (=U.S. Ser.No. 651,234, filed May 31, 1990) (immunomodulator), U.S. Pat. No. 4,107,310 (analgetics) and JP 68023948 (bacteriocides). U.S. patents and patent applications given above are hereby incorporated by reference. In general it can be stated that many of the compounds comprising structure I are classified as immune modulators with individual effects spanning the spectra from suppression to stimulation of the immune system. The specific effect achieved depends on the substituents.

One of the most important compounds with formula I is the 1,2-dihydro-hydroquinoline-3-carboxamides, particularly N-phenyl-N-methyl-1,2-dihydro-4-hydroxy-1-methyl-2-oxo-quinoline-3-carboxamide roquinimex (Linomide®), i.e. structures I and II with a substituent for $H^1$ that equals phenyl, for $H^2$ that equals methyl, for $H^8$ that equals methyl (attached to the nitrogen atom of the quinoline ring), with no substituents for $H^{3-7}$, with $H^7$ attached to $X_1$, and with each of $X_1$ and $X_2$ equalling an oxygen atom. The compound has double bonds between positions 3 and 4 and between positions 2 and $X_2$.

The scientific experimentation with roquinimex has shown that roquinimex has multiple immunological activities. It has thus been found that roquinimex increases the proliferative response to T- and B-cell mitogens [28], enhances antibody production [29] and augments NK cell activity [30, 31]. Moreover, its immunostimulating and immunoregulating properties may be useful in the treatment of tumours [32] and systemic lupus erythematosis [33, 34] as suggested in U.S. Pat. Nos. 4,547,511 and 4,738,971.

Published PCT-application WO 91/12804 discloses roquinimex as a drug for the treatment of retrovirus infections. WO 91/14432 discloses roquinimex as a drug for regenerating lymphoid cells in patients treated with autologous bone marrow transplantation. WO 93/06829 discloses roquinimex as a drug for the treatment of multiple sclerosis. These published patent applications are hereby incorporated by reference.

OBJECTS OF THE INVENTION

One major objective of the invention is to provide a method for inhibiting the production of tumour necrosis factor (TNF) in a living body or for treating a living body in danger of producing TNF. A second major objective of the invention is to provide a method for treatment of septic shock in a living body or for treatment of a living body in danger of acquiring septic shock. Further objectives are to provide drugs to be used for the manufacture of pharmaceutical compositions for the treatment of the conditions given in the preceding sentences.

In Scand. J. Infect. Dis., suppl. 88, volume April 1993, Nils-Gunnar Ilbäck et al. "Effects of the Antiviral WIN 54954 and the Immune Modulator LS 2616 on Cachectin/TNF and the Gamma-interferon Responses during Viral Heart Disease", page 117–123, certain effects of roquinimex are discussed.

Anyhow, the TNF production in the described viral model is dependent on viral load, for example a response to the virus infection. Roquinimex has been shown to inhibit coxsackie-B infection. Since both the antiviral WIN 54954 and roquinimex affect TNF levels, the effect on TNF is likely to be secondary to the effect on viraemia—not a direct inhibitory effect on TNF. This is also reflected in the kinetics of the roquinimex effect: although roquinimex was given from day 5 before infection with virus it had no effect on TNF in the early phase of viraemia. In contrast, its peak effect was identical in time to that of WIN 54954.

THE INVENTION

It has unexpectedly been found that roquinimex displays a marked anti-apoptotic effect related to an inhibition of the secretion of the tumour necrosis factor (TNF). Apoptosis is equivalent to programmed cell death. The anti-apoptotic effect thus implies the antagonization of programmed cell death.

The above mechanism is fundamentally different from hitherto known mechanisms of roquinimex and can be used to inhibit the production of TNF and/or to treat septic shock. Below are described four models of septic shock and tests undertaken to evaluate the effects of roquinimex and other drugs on these models.

The susceptibility of rodents to the lethal effect of endo- and exotoxins can be augmented by means of two different strategies, namely the simultaneous injection of D-galactosamine (GalN), an inhibitor of mRNA synthesis [2], or by withdrawal of endogenous GC either by bilateral adrenalectomy or by injection of saturating amounts of the antiglucocorticoid RU-38486 (mifepristone) [10, 11]. The mode of action of both sensitizing agents implies an increase in the production of TNF induced by GalN [12] or, alternatively, an increased susceptibility to the lethal effect of TNF that is caused by withdrawal of endogenous GC [13, 14].

The bacterial superantigen *Staphylococcus aureus* enterotoxin B (SEB) induces the apoptotic death of SEB-reactive T-cells expressing products of the TCR $V_\beta 8$ gene family ($V_\beta 8.1-3$) [15, 16]. In addition, both sensitizing agents GalN and RU-38486 have been found to induce apoptosis in $CD4^+$ and $CD8^+$ peripheral T-cells. These findings prompt the hypothesis that a massive apoptotic decay of lymphocytes contributes to the lethal effect of polyclonal stimuli [11]. It has been demonstrated that the immunomodulator roquinimex displays a marked anti-apoptotic effect on peripheral B- and T-lymphocytes (Gonzalo et al submitted). In the present application is shown that roquinimex prevents the lethal effect of four different combinations of polyclonal stimulators and sensitizing agents, namely LPS+GalN, LPS+RU-38486, SEB+GalN and SEB+RU-38486.

Roquinimex may be used as such or as a pharmaceutically acceptable salt thereof. Furthermore, roquinimex can be used in combination with other agents. Formulations that could be used according to the present invention are disclosed in U.S. Pat. No. 4,547,511 col. 11.

Material and Methods

Animals and in vivo manipulations: 8 to 12-week-old male BALB/c mice were injected with the exotoxin *Staphylococcus aureaus* enterotoxin B (SEB, 50 µg/200 µl PBS i.v.; Sigma, St Louis, Mo.), the endotoxin lipopolysaccaride (LPS from *E. Coli*, 50 µg/200 µl PBS i.v.; Sigma), the GC receptor antagonist RU-38586 (kindly provided by Dr. Martini, Roussel Uclaf, Romainville, France; 10 mg/200 µl PBS i.p.), dexamethasone (DEX, 1 mg/200 µl PBS, i.p.) cyclosporin A (0.5 mg/200 µl PBS i.p.; Sandoz, Basel, Switzerland) and/or received treatment with roquinimex (LS 2616, Kabi Pharmacia AB, Helsingborg, Sweden; batch: AU PC003; 100 mg/kg/d supplied in the drinking water 2 days before injection of SEB) at doses found to be optimal in preliminary experiments. Reagents and vehicle controls (PBS i.v. and i.p.) were administered simultaneously with LPS or SEB.

Quantitation of TNF. BALB/c mice were injected with SEB (50 µg i.v.), D-galactosamine (20 mg i.p. together with SEB), RU 38486 (10 mg i.p. together with SEB) and/or DEX (1 mg, 2 hours prior to SEB-injection) and/or received roquinimex (300 mg/kg/d per os starting from day 2 before SEB). Animals (3–4/group) were sacrificed 2 hours after SEB injection when TNF serum levels are maximal, and TNF was quantified by ELISA following the manufacturer's protocol (Genzyme). In addition, splenocytes ($2 \times 10^5$ ml) from animals receiving roquinimex for 5 days (0.1 to 1 g/kg/d per os) were cultured for 48 hours in culture medium (RPMI 1640 supplemented with 10% foetal calf serum, 50 µM 2-mercaptoethanol, 10 mM Hepes, 200 µM L-glutamine, 10 U/ml penicillin and 100 µg/ml streptomycin) in the absence or presence of 10 µg/ml SEB, followed by determination of TNF concentrations in the conditioned medium (CM).

RESULTS

Example 1

Roquinimex inhibits acute death in response to LPS

If injected intravenously at a dose of 50 µg LPS fails to kill BALB/c mice, unless administered together with sensitizing agents like GalN or RU-38486, each of which is used at doses that per se are not toxic. In both models, co-administration of synthetic GC agonist dexamethasone (DEX) abrogates lethality, thus confirming the critical role of GC in determining the toxicity of polyclonal stimuli. Whereas the T-cell targeted inhibitor cyclosporine A (CsA) failed to exert a life-preserving effect with LPS+GalN or LPS+RU-38486, continuous administration of roquinimex rescued animals from death.

The results from the above tests are presented in FIG. 1 and can be summarized as follows:

Roquinimex abrogates the acute toxicity of LPS. Mortality rates of mice receiving LPS together with different treatments are shown. Asterisks mark significant ($p<0.01$, Chi square analysis) effects of roquinimex when compared to the respective control group not receiving roquinimex. Black boxes indicate the administration of the corresponding drug. Doses are indicated in Materials and methods. Deaths occurred within a period of 16–36 hours upon injection of LPS after displaying pilierection, hypothermia and bradycardia.

Example 2

Roquinimex prevents death in response to SEB. As is true for LPS two different strategies augment the sensitivity of mice to SEB toxicity, namely the co-administration of D-galactosamine [2] and the abolition of the effect of endogenous GC either by injection of saturating [17] amounts of the GC antagonist RU-38486 or adrenalectomy [11]. In these two models for acute lethal septic shock (SEB+RU-38486 or SEB+GalN) three pharmacological interventions were found to be life-preserving, namely injection of high doses of DEX (1 mg), cyclosporin A (CsA) [2], and treatment with roquinimex. Roquinimex did not induce an increase in GC levels (data not shown) and was effective in the presence of an excess [17, 18] of the GC receptor antagonist RU-38486, indicating that its molecular and/or cellular mode of action differs from that of GC. Furthermore, its mechanism of action must differ from that of CsA, which although effective with SEB+RU-38486 or SEB+GalN fails to abolish the lethal effect of LPS+RU-38486 or LPS+GalN (vide supra).

Figure 2:
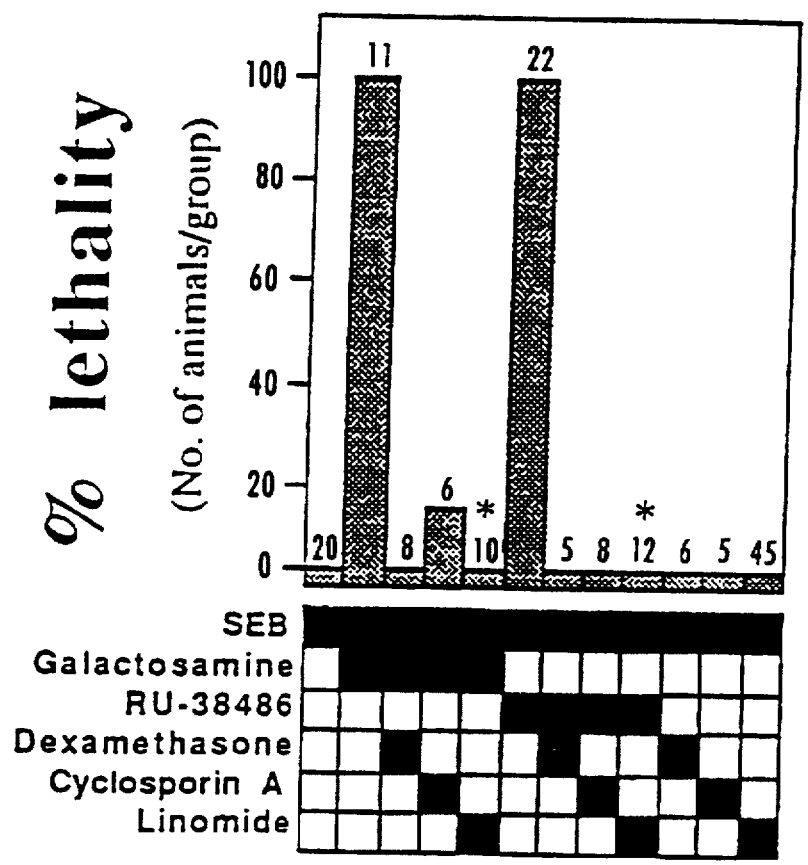

The results from the above tests are presented in FIG. 2 and can be summarized as follows:

Roquinimex abrogates the acute toxicity of exotoxin. Asterisks mark significant ($p<0.01$) effects of roquinimex when compared to the respective control group not receiving roquinimex. Black boxes indicate the administration of the corresponding drug. Doses are indicated in Materials and methods. All deaths occurred within a period of 16–36 hours after injection of SEB. In contrast to LPS-injected animals (FIG. 1) diarrhoea was observed after injection of the toxin.

Example 3

Roquinimex reduces the SEB-induced secretion of TNF in vivo and ex vivo. Septic shock involves a cytokine release syndrome due to a hyperacute activation of inflammatory cells [3], TNF being one of the major intermediate pathogenic factors that causes death in response to SEB [2] or LPS [6, 7]. It was shown that the life-preserving effect of roquinimex may be related to a partial inhibition of SEB-driven TNF production. Although GalN does not induce TNF production by itself it significantly enhances the TNF serum detected shortly (120 min.) after SEB injection. This is not true for RU-38486 that sensitizes to the toxic effect of TNF [14]. Roquinimex-treated animals exhibited lowered TNF production in response to SEB as compared to controls, irrespective of whether SEB was administered alone or in combination with GAlN or RU-38486. The inhibition of TNF-production could also be detected in splenic T-cells recovered from roquinimex-treated animals ex vivo.

Figures 3, 3A:
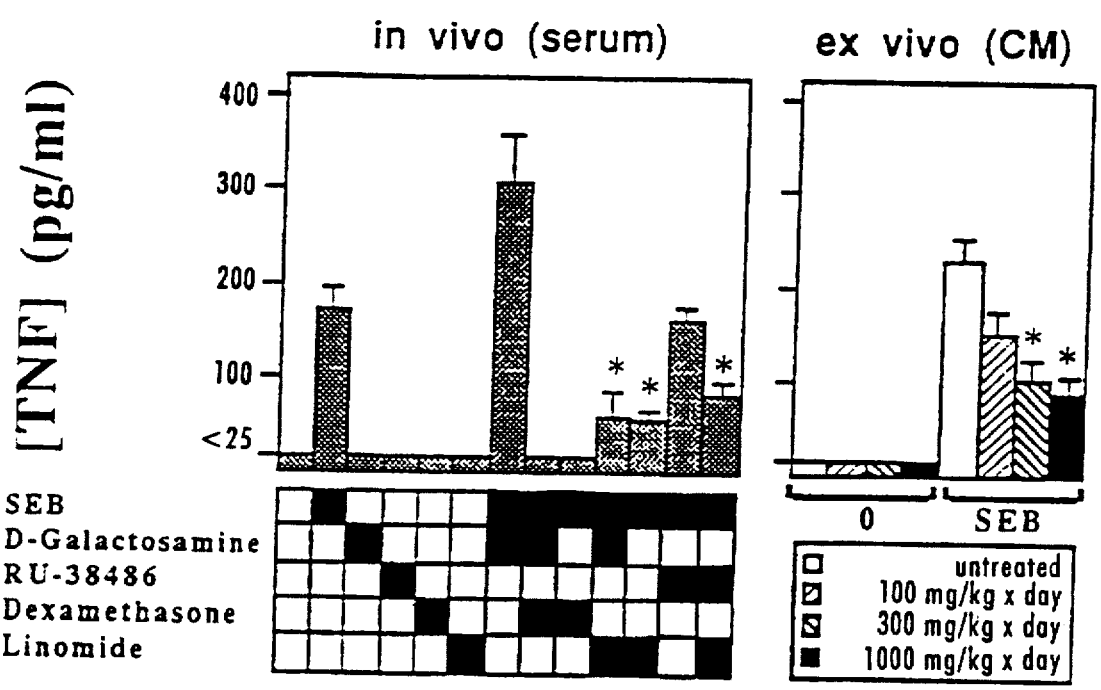

The results from the above tests are presented in FIG. 3 and can be summarized as follows:

Roquinimex inhibits the production of TNF in vivo. TNF concentrations were measured in the serum of animals injected 2 hours before with SEB and receiving additional (pre)treatments. In addition the in vitro secretion (48 h) of TNF by SEB-stimulated splenocytes obtained from roquinimex-pretreated animals (doses in mg/kg/d) was determined. Black squares mark the corresponding in vivo treatment. Asterisks indicate significant ($p<0.01$) effects of roquinimex.

As shown above roquinimex abolishes the lethal effect of combined injections of LPS+GalN, LPS+RU-38486, SEB+GalN and SEB+RU-28486, a fact that is probably related to an inhibition of TNF-production. Roquinimex, a mediator that antagonizes immunosuppressive CsA effects in vivo [19, 20], has a similar effect as CsA on SEB toxicity. In contrast to CsA, roquinimex extends its life-rescuing effect to LPS-mediated septic shock. Although roquinimex has an effect similar to that of exogenous GC on SEB and LPS toxicity it is a functional GC antagonist in other systems, for example abolishing the DEX-induced apoptosis and numeric depletion of mature splenic T-lymphocytes (Gonzalo et al submitted for publication). Together these findings indicate that the molecular and/or cellular mode of action of roquinimex differs from that of known immunosuppressive agents like GC or CsA. In vivo injection of SEB, RU-38486 or GalN has been shown to induce programmed cell death of $CD^{4+}$ and $CD^{8+}$ lymphocytes [11, 15, 16], a fact that might contribute to their toxicity. It is tempting to link the life-preserving effect of roquinimex to its anti-apoptotic effect, which, in turn, might be related to an inhibition of the secretion of TNF, a mediator that induces apoptosis in a variety of target cells [5, 21].

As septic shock is a severe disease with high lethality it is desirable to start treating the patients at a very early stage, preferably before the appearance of any acute symptoms. Elastase is considered an early indicator of septicemia [22, 23, 24, 25, 26, 27]. The plasma level of neutrophil elastase, like protease complexed to $a_1$ antitrypsin ($a_1$ AT-ELP), has been shown to be significantly increased in septic patients as compared to non-septic patients [22]. Using early indicators like elastase makes it possible to treat even patients in danger of acquiring septic shock.

References

1. Marrack, P., Blackman, M., Kushnir, E. and Kappler, J., *J. Exp. Med.* 1990. 171:455–464.

2. Miethke, T., Wahl, C., Heeg, K., Echtenacher, B., Krammer, P. H. and Wagner, H., *J. Exp. Med.* 1992. 175:91–98.

3. Glauser, M. P., Zanetti, G., Baumgartner, J. D. and Cohen, J., *Lancet* 1991. ü:732–739.

4. Cohen, J. and Glauser, M. P., *Lancet* 1991. ü:736–739.

5. Vassalli, P., *Ann. Rev. Immunol.* 1992. 10:411–452.

6. Beutler, B., Milsark, I. W. and Cerami, A. C., *Science* 1985. 229:869–871.

7. Tracey, K. J., Fong, Y., Hesse, D. G., Manogue, K. R., Lee, A. T. and Kuo, G. C., *Nature* 1987. 330:662–664.

8. Tzung, S.-P., Mahl, T. C., Lance, P., Andersen, V. and Cohen, S. A., *Eur. J Immunol.* 1992. 22:3097–3101.

9. Gérard, C., Bruyns, C., Marchant, A., Abramowicz, D., Vandenabeele, P., Delvaux, A., Fiers, W., Goldman, M. and Valu, T., *J. Exp. Med.* 1993. 177:547–550.

10. Perretti, M., Becherucci, C., Scpapigliati, G. and Parente, L., *Br. J. Pharmacol.* 1989. 98:1137–1142.

11. Gonzalo, J. A., González-Garcia, A., Martinez-A., C. and Kroemer, G., *J. Exp. Med.* 1993. in press:

12. Alegre, M.-L., Vandenabeele, P., Depierreux, M., Florquin, S., Deschodt-Lanckman, M., Flamand, V., Moserm N, Leo, O., Urbain, J., Fiers, W. and Goldman, M., *J. Immunol.* 1991. 146:1184–1191.

13. Bertini, R., Bianchi, M. and Ghezzi, P., *J. Exp. Med.* 1988. 167:1708–1712.

14. Brouckaert, P., Everaerdt, B. and Fiers, W., *Eur. J. Immunol.* 1992. 22:981–986.

15. Kawabe, Y. and Ochi, A., *Nature* 1991. 349:245–248.

16. Gonzalo, J. A., Moreno de Alborán, I., Alés-Martinez, J. E., Martinez-A., C. and Kroemer, G., *Eur. J Immunol.* 1992. 22:1007–1011.

17. Van Voorhis, B. J., Anderson, D. J. and Hill, J. A., *J. Clin. Endocrinol. Metab.* 1989. 69:1195–1199.

18. Alexandrova, M., *J. Steroid Biochem. Mol. Bio.* 1992. 41:723–725.

19. Wanders, A., Larsson, E., Gerdin, B. and Tufveson, G., *Transpl.* 1989. 47:216–217.

20. Wanders, A., Vogt, P., Karlsson-Parra, A., Wonigkeit, K., Gerdin, B. and Tufveson, G., *Transplantation* 1991. 52:234–238.

21. Heller, R. A., Song, K., Fan, N. and Chang, D. J., *Cell.* 1992. 70:47–56.

22. Seitz, R., Wolf, M., Egbring, R., Radtke, K.-P., Liesenfeld, A., Pittner, P. and Havemann, K., *Eur. J. Haematol* 1987; 38:231–240.

23. Speer, C., Rethwilm, M. and Gahr, M., *The Journal of Pediatrics*, November 1987, 667–671.

24. Ericsson-Hollsing, A., Lantz, B., Bergström, K., Malmborg, A. and Strandvik, B., *The Journal of Pediatrics*, August 1987, 206–211.

25. Adeyemi, E. O., D'Anastasio, C., Impallomeni, M. and Hodgson, H. J. F., *Aging*, 1989, Vol. 1, N. 1, 65–70.

26. Egbring, R., Seitz, R., Blanke, H., Leititis, J., Kesper, H. J., Burghard, G., Fuchs, G. and Lerch, L., *Behring Inst. Mitt.*, 1986, No 79, 87–103.

27. Jochim, M., Witte, J., Duswald, K.-H., Inthom, D., Welter, H. and Fritz, H., *Behring Inst. Mitt.*, 1986, No 79, 121–130.

28. Larsson, E. L. et al, *Int. J. Immunopharmacol*, 1987;9:425.

29. Carlsten H., et al. *APMIS* 1989;97:728.

30. Kalland, T., et al., *J. Immunol.* 1985;134:3956

31. Kalland, T., *J. Immunol.*1990;144:4472.

32. Kalland, T., *Cancer Res.*, 1986;46:3018.

33. Tarkowski, A. et al., *Immunology* 1986;59:589.

34. Tarkowski, A. et al., *Arthrit Rhemat*, 1986;29:1405.

We claim:

1. Method for inhibiting the production of tumour necrosis factor (TNF) in a living body suffering from said production by administration of an effective amount of a quinoline-3-carboxamide compound or a pharmaceutically acceptable salt thereof to a living body suffering from said production, wherein said compound comprises the structure 1, optionally with substituents for the hydrogen atoms shown ($H^{1-9}$)

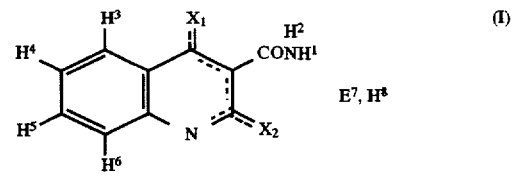

where (a) ----- represents that there are two conjugated double bonds bonds between the atoms comprised by the dashed line, (b) $X_1$ and $X_2$ are separately selected from an oxygen atom or an $NH^9$ group, said $X_1$ and $X_2$ being bound by a single bond to the ring when attached to $H^7$ or $H^8$ and by a double bond when not bound to $H^7$ or $H^8$.

(c) $H^{1-9}$ are hydrogens, with the provision that $H^9$ is only present when at least one of $X_1$ and $X_2$ is $NH^9$ group, (d) $H^7$ and $H^8$ are hydrogens that are attached to different atoms selected among $X_1$, $X_2$ and the nitrogen atom (N) in the quinoline ring.

2. Method according to claim 1 wherein the compound is N-phenyl-N-methyl-1,2-dihydro-4-hydroxy-1-methyl-2-oxo-quinoline-3-carboxamide.

3. The method as claimed in claim 1 wherein said administration is accomplished orally.

4. The method as claimed in claim 1 wherein said administration is accomplished by injection.

5. The method as claimed in claim 1 wherein said administration is accomplished parentally.

* * * * *